US009238095B2

(12) United States Patent
Teraura et al.

(10) Patent No.: US 9,238,095 B2
(45) Date of Patent: Jan. 19, 2016

(54) ADAPTER AND CONNECTION STRUCTURE

(75) Inventors: Makoto Teraura, Takarazuka (JP); Kazutaka Yoshino, Takarazuka (JP)

(73) Assignee: HI-LEX CORPORATION, Hyogo (JP)

( * ) Notice: Subject to any disclaimer, the term of this patent is extended or adjusted under 35 U.S.C. 154(b) by 435 days.

(21) Appl. No.: 13/643,383

(22) PCT Filed: Apr. 28, 2011

(86) PCT No.: PCT/JP2011/060407
§ 371 (c)(1),
(2), (4) Date: Jan. 4, 2013

(87) PCT Pub. No.: WO2011/136346
PCT Pub. Date: Nov. 3, 2011

(65) Prior Publication Data
US 2013/0133944 A1    May 30, 2013

(30) Foreign Application Priority Data

Apr. 28, 2010  (JP) ................................. 2010-104385

(51) Int. Cl.
*H02G 15/08*    (2006.01)
*A61M 1/12*    (2006.01)
(Continued)

(52) U.S. Cl.
CPC ............. *A61M 1/127* (2013.01); *A61M 1/1008* (2014.02); *A61M 39/105* (2013.01); *F16L 39/00* (2013.01); *F16L 39/02* (2013.01); *H02G 15/08* (2013.01)

(58) Field of Classification Search
CPC ................................ H02G 15/08; A61M 1/127
USPC ........... 174/72 R, 20; 604/247, 534; 128/349, 128/692
See application file for complete search history.

(56) References Cited

U.S. PATENT DOCUMENTS 3,333,045 A * 7/1967 Fisher et al. .................... 174/20
4,329,994 A * 5/1982 Cooper ....................... 604/98.01
(Continued)

FOREIGN PATENT DOCUMENTS

DE  3903565 A1  8/1990
JP  59-137712 U  9/1984
(Continued)

OTHER PUBLICATIONS

International Search Report of corresponding International Application No. PCT/JP2011/060407, dated on Jul. 26, 2011.

*Primary Examiner* — Timothy Thompson
*Assistant Examiner* — Michael F McAllister
(74) *Attorney, Agent, or Firm* — Global IP Counselors, LLP

(57) ABSTRACT

An adapter and its connection structure having a plurality of tubes bundled together as one that can be connected to be made shorter in the diameter direction to transport fluid to and from artificial organs and connect electric wires to the artificial organs without changing design of the artificial organs. The adapter and connecting structure connect multi-lumen and single tubes so their passages communicate with each other. The first attachment member, attached to the multi-lumen tube, includes first ports having an outer diameter substantially the same a lumen opening diameter at the end portion of the multi-lumen tube to fit into the lumen openings, and a first cutout corresponding to one of the lumen openings. The second attachment member, attached to the single tube, includes second ports that fit into the lumen of the single tube. The number of the first and second ports is the same.

17 Claims, 5 Drawing Sheets

(51) Int. Cl.
*A61M 39/10* (2006.01)
*F16L 39/00* (2006.01)
*F16L 39/02* (2006.01)
*A61M 1/10* (2006.01)
*A61M 5/00* (2006.01)

(56) References Cited

U.S. PATENT DOCUMENTS

| | | | |
|---|---|---|---|
| 4,718,423 A * | 1/1988 | Willis et al. | 600/325 |
| 4,817,624 A * | 4/1989 | Newbower | 600/505 |
| 5,995,208 A * | 11/1999 | Sarge et al. | 356/39 |
| 2005/0256461 A1 * | 11/2005 | DiFiore et al. | 604/247 |
| 2005/0267445 A1 * | 12/2005 | Mendels | 604/534 |
| 2009/0051161 A1 | 2/2009 | Ekstrom | |

FOREIGN PATENT DOCUMENTS

| | | |
|---|---|---|
| JP | 2000-325469 A | 11/2000 |
| JP | 2002-081315 A | 3/2002 |
| JP | 2003-116889 A | 4/2003 |
| JP | 2009-525442 A | 7/2009 |
| WO | WO-2009/103758 A2 | 8/2009 |

* cited by examiner (a)

(b)

(c)

(a)

(b)

(a)        (b)

(a)        (b)

ADAPTER AND CONNECTION STRUCTURE

CROSS-REFERENCE TO RELATED APPLICATIONS

This U.S. National stage application claims priority under 35 U.S.C. §119(a) to Japanese Patent Application No. 2010-104385, filed in Japan on Apr. 28, 2010, the entire contents of Japanese Patent Application No. 2010-1043855 are hereby incorporated herein by reference.

BACKGROUND

1. Field of the Invention

The present invention relates to an adapter for connecting a multi-lumen tube, consisting of one tube having a plurality of lumens, with a single tube including a single passage. The present invention further relates to a connection structure through which electric wires, inserted into the lumens of the multi-lumen tube to be connected to the adapter, are led out to a product to be electrically connected.

2. Background Information

Concerning medical devices, artificial organs used as replacement of human organs, such as artificial kidneys, artificial hearts, and etc., have been known. The artificial hearts include stationary artificial hearts, implantable artificial hearts to be implanted into human bodies, and auxiliary artificial hearts, for example. In the implantable artificial hearts, a plurality of tubes lead into the human bodies from the outside, such as electric wires for delivering electricity for driving the artificial hearts and cylindrical tubes for transporting fluid to/from the implanted artificial hearts.

When the plurality of tubes are inserted into the human body, the human body shall have a plurality of inserting openings, which puts the patient under strain. In order to decrease the strain, as described in the Japanese Patent Laid-Open Publication No. 2000-325469, a tube unit has been proposed, which includes one outer tube into which the power cables and the plural tubes are built.

SUMMARY OF THE INVENTION

However, if the tubes are built into the outer tube as they are, the cylindrical tubes make point contacts with each other in the diameter direction. Accordingly, dead spaces occur in the diameter direction, so that the diameter of the tube unit increases. This may cause the human body to be under strain. Therefore, it may be thought of using a multi-lumen tube including a plurality of lumens extending in the axial direction, in which the lumens have an oddly formed or deformed transverse section. However, if the multi-lumen tube is used as it is, because the multi-lumen tube cannot divide a flow passage by itself without other devices, it will be necessary to change the device design of the artificial organs in order to allow the fluid to flow in and out, e.g. by placing an inflow opening and a discharge opening in adjacent positions.

Accordingly, it is an object of the present invention to provide an adapter and a connection structure using the adapter, in which a plurality of tubes are bundled together as one and the tubes introduced into the human body from outside can be made shorter in the diameter direction, so that it is possible to transport the fluid to and from the artificial organs and to connect the electric wires to the artificial organs without changing design of the artificial organs, thereby reducing the strain on the human body.

The present invention is an adapter for connecting a multi-lumen tube and a single tube such that passages of the multi-lumen tube and the single tube communicate with each other. The multi-lumen tube includes a plurality of lumens extending in the axial direction. The transverse section of the lumens is oddly formed or deformed, and the single tube has a single passage. The adapter includes a first attachment member to which the multi-lumen tube is attached, and a second attachment member to which the single tube is attached. The first attachment member includes a plurality of first ports having an outer diameter substantially the same as that of a lumen opening at the end portion of the multi-lumen tube, and a first cutout. The first ports are positioned such that the first ports can fit into the lumen openings when the multi-lumen tube is attached to the first attachment member, and the first cutout is formed in a way so as to correspond to one of the lumen openings when the multi-lumen tube is attached to the first attachment member. The second attachment member includes second ports configured to fit into the lumen of the single tube. The number of the second ports is the same as that of the first ports.

The present invention is a connection structure for a medical device including a driving section. The connection structure comprises an adapter as described above. The multi-lumen tube includes a first lumen, a second lumen, and a third lumen. The first lumen and the second lumen are formed such that a cooling medium for the driving section can flow therethrough, and the third lumen contains electric wires therein. The connection structure comprises two tubes as the single tube through which the cooling medium can flow. The first lumen and the second lumen communicate with respectively the single tubes such that the cooling medium can flow therethrough. The electric wires are led out from the first cutout to a product to be electrically connected.

Using an adapter according to the present invention, the fluid passage through which the liquid flows into and out of the artificial organs can be provided without resulting in any dead space. In addition, since the fluid passages for the liquid can communicate with the single tubes, the tube can have a decrease in the diameter, thereby decreasing the strain on the human bodies. Furthermore, it is possible to easily connect the adapter with the artificial organs without changing the design of the artificial organs.

BRIEF DESCRIPTION OF DRAWINGS

FIG. 1 (b) is a transverse view of the multi-lumen tube in FIG. 1 (a);

FIG. 1 (c) is a partially enlarged perspective view of a single tube used for an adapter according to the present invention;

FIG. 2 (b) is an assembly drawing of an adapter in FIG. 2 (a);

FIG. 3 (b) is a perspective view of the first attachment member in FIG. 3 (a) seen from the first opening portion side;

FIG. 4 (b) is a perspective view of the second attachment member in FIG. 4 (a) seen from the second port side;

FIG. 6 (b) is an assembly figure of the adapter in FIG. 6 (a).

DETAILED DESCRIPTION OF EMBODIMENTS

Figure 1:
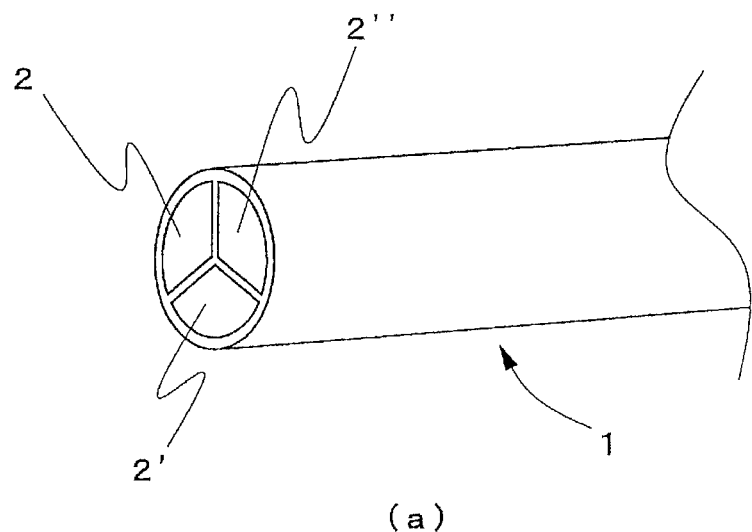
FIG. 1 (a) is a partially enlarged perspective view of one embodiment of the multi-lumen tube used for an adapter according to the present invention.
Figure 1:
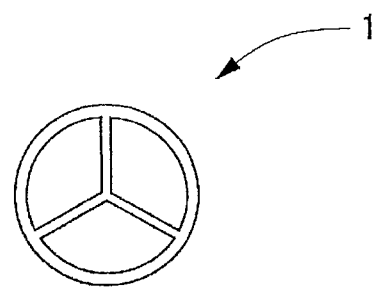
Figure 1:
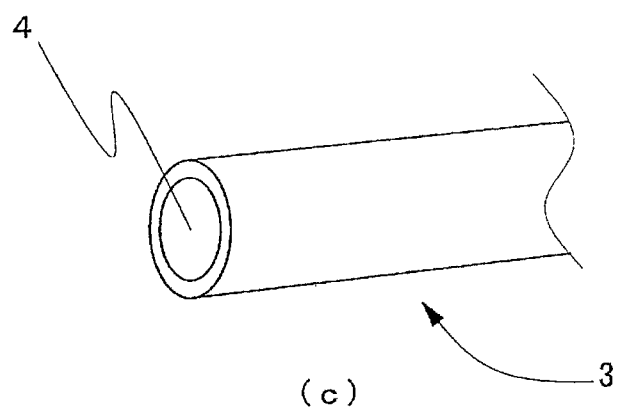

Hereinafter, although the present invention will be explained referring to the drawings, the present invention is not limited to the explanation below. The adapter according to the present invention employs a multi-lumen tube for bundling the tubes together and decreasing the diameter of the tubes. FIG. 1(a) is a partially enlarged perspective view of a tip section of one embodiment of the multi-lumen tube. FIG. 1(b) is a transverse section of the multi-lumen tube in FIG. 1(a). The multi-lumen tube 1 includes, as shown in FIG. 1(a), three lumens extending in the axial direction. In the multi-lumen tube 1 of the present embodiment, the lumens are equally divided with a transverse section of a fan shape. Each of lumen openings 2, 2', and 2" at the end portion have a fan shape of about 120 degrees. Compared to a circular sectional shape, since there is no thick portion between these lumens, it is possible to decrease the diameter of the multi-lumen tube. It should be noticed that a single tube to be connected to the adapter according to the present invention includes, as shown in FIG. 1(c), one lumen as a single tube.

FIG. 2(a) is a perspective view of one embodiment of an adapter according to the present invention. FIG. 2(b) is an assembly drawing of the adapter in FIG. 2(a). The adapter 10 includes, as shown in FIG. 2(b), a first attachment member 20, a packing 30, a second attachment member 40, and a fixing member 50. The first attachment member 20 is a member to which the multi-lumen tube is attached. The second attachment member 40 is a member to which the single tubes are attached. The first attachment member 20 includes first ports 21 and 22. The first ports 21 and 22 have substantially the same shape of outer diameters as that of lumen openings 2 and 2' at the end portion of the multi-lumen tube 1, so that the first ports 21 and 22 respectively fit into the lumen openings 2 and 2'. The first ports 21 and 22 are positioned such that when the multi-lumen tube 1 is attached, the first ports 21 and 22 can fit into the lumen openings 2 and 2' respectively. The adapter 10 is, after assembled, connected to the multi-lumen tube 1 by inserting the two first ports 21 and 22 into the lumen openings 2 and 2' of the multi-lumen tube 1

It should be noticed that the outer shape of the first ports 21 and 22 may be substantially the same as that of the lumen openings as long as the first ports 21 and 22 may fit into the lumen openings in a liquid-tight state. The outer shape of the first ports 21 and 22 may be substantially elliptic, being deformed from the same shape of the lumen openings. In other words, the first ports 21 and 22 do not have to have a fan shape.

In addition, a first base portion 23 of the first attachment member 20 is formed with a first cutout 26, which is located at a position corresponding to the remaining one lumen 2" of the multi-lumen tube. When the first ports 21 and 22 are inserted into two lumens of the multi-lumen tube 1, the end of lumen opening 2", as the remaining lumen, gets into contact with the first cutout 26. Accordingly, it is not necessary to considerably bend the electric wire inserted into the lumen in order to bypass the first base portion 23. In other words, it is easy to lead the electric wire out from the adapter through the lumen opening 2" and the first cutout 26.

The second attachment member 40 includes a same number of second ports 41 and 42 as that of the first ports 21 and 22. The second ports 41 and 42 are inserted into the lumens 4 of two single tubes 3, so that the adapter 10 is connected to the two single tubes 3.

Figure 3:
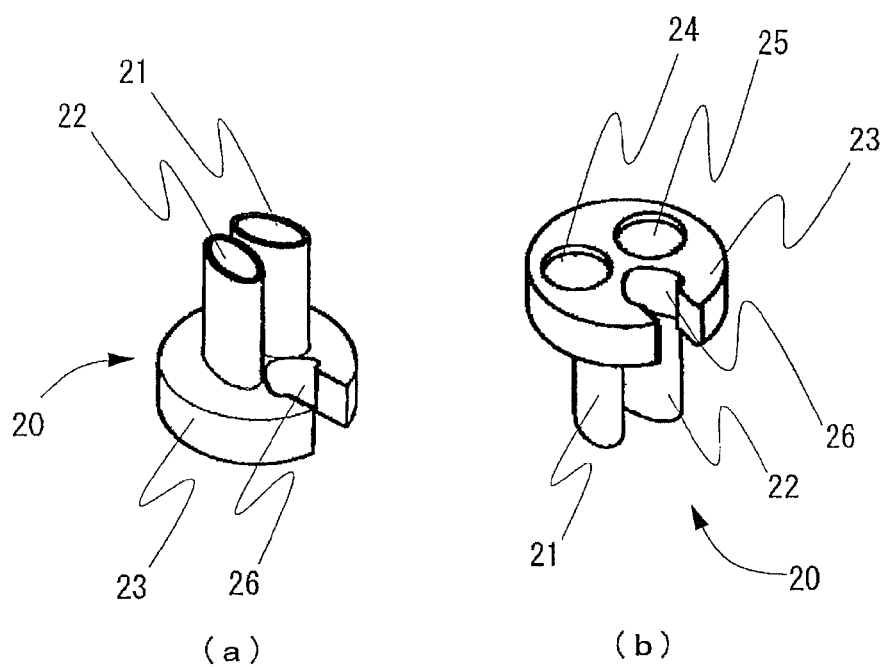
FIG. 3 (a) is a perspective view of the first attachment member seen from the first port side.

The first attachment member 20 includes, as shown in FIG. 3(a) and FIG. 3(b), the first ports 21 and 22 at the first base portion 23. The first base portion 23 includes a surface on which the first ports 21 and 22 are provided, and an opposite surface formed with first opening portions 24 and 25 for connecting with the first ports 21 and 22, respectively. The second attachment member 40 includes, as shown in FIG. 4(a) and FIG. 4(b), the second ports 41 and 42 at a second base portion 43. The second base portion 43 includes a surface on which the second ports 41 and 42 are provided and an opposite surface formed with second openings 44 and 45 connected with the second ports 41 and 42.

Figure 4:
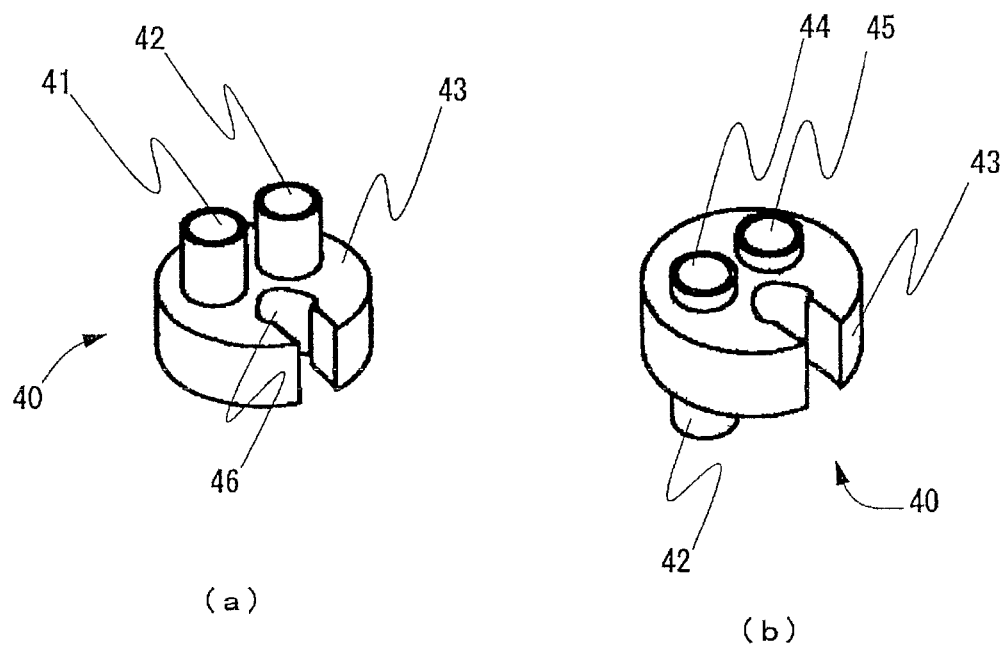
FIG. 4 (a) is a perspective view of the second attachment member seen from the second port side.

According to an embodiment shown in FIG. 4, the second openings 44 and 45 are formed as tubular projections for fitting into the first opening portions 24 and 25. In addition, since the first attachment member 20 and the second attachment member 40 are provided such that the first opening portions 24 and 25 correspond to the second openings 44 and 45, respectively, it is possible to easily connect the first opening portions 24 and 25 with the second openings 44 and 45 respectively by providing the first opening portions 24 and 25 and the second openings 44 and 45 so as to correspond to each other. Accordingly, it is also possible to easily communicate the first ports 21 and 22 with the second ports 41 and 42. This structure allows the multi-lumen tube 1 to be connected with the single tubes 3 in a way that the passages of them communicate with each other.

In an embodiment shown in FIG. 2, the assembly of the adapter 10 will be explained. In the assembly, the first attachment member 20 and the second attachment member 40 are connected with each other via a packing 30 such that the first base portion 23 and the second base portion 43 substantially become one single unit. When the multi-lumen tube 1 is connected to the single tubes 3 in a way that the passages of them communicate with each other, the fixing member 50 fixes the first attachment member 20 to the second attachment member 40 while covering the first base portion 23 and the second base portion 43. During this time, it is preferable that the second attachment member, which has a spiral male thread (not shown) formed around the second base portion 43, is screwed with the fixing member, which has a female thread (not shown) screwable with the male thread, thereby fixing the first attachment member 20 to the second attachment member 40. This simple way of fixing allows the adapter to be easily assembled. In addition, since the second openings 44 and 45 are formed as tubular projections, it is possible to easily assemble the adapter 10 such that the first opening portions and the second openings are joined. In addition, since these projections are provided, even if a lateral force is applied, the projections receive the force, so that it is unlikely for the first attachment member and the second attachment member to be disengaged from each other.

Figure 2:
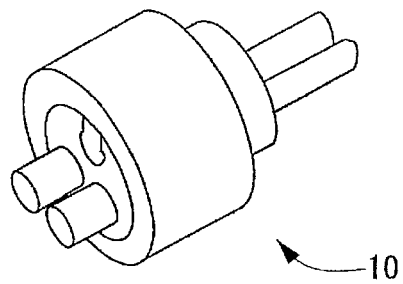
FIG. 2 (a) is a perspective view of one embodiment of an adapter according to the present invention.
Figure 2:
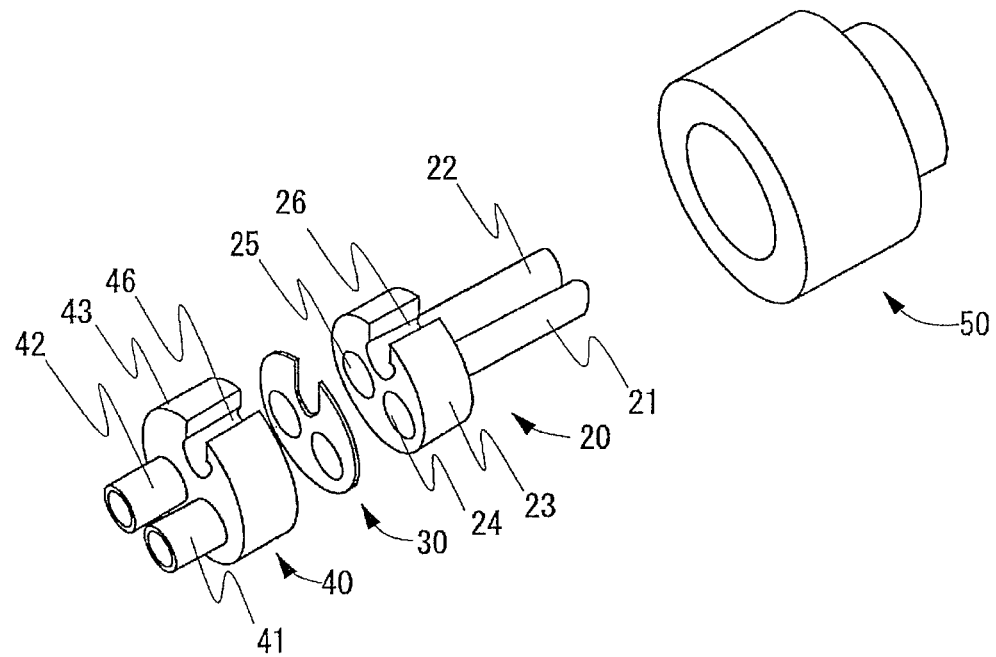
Figure 5:
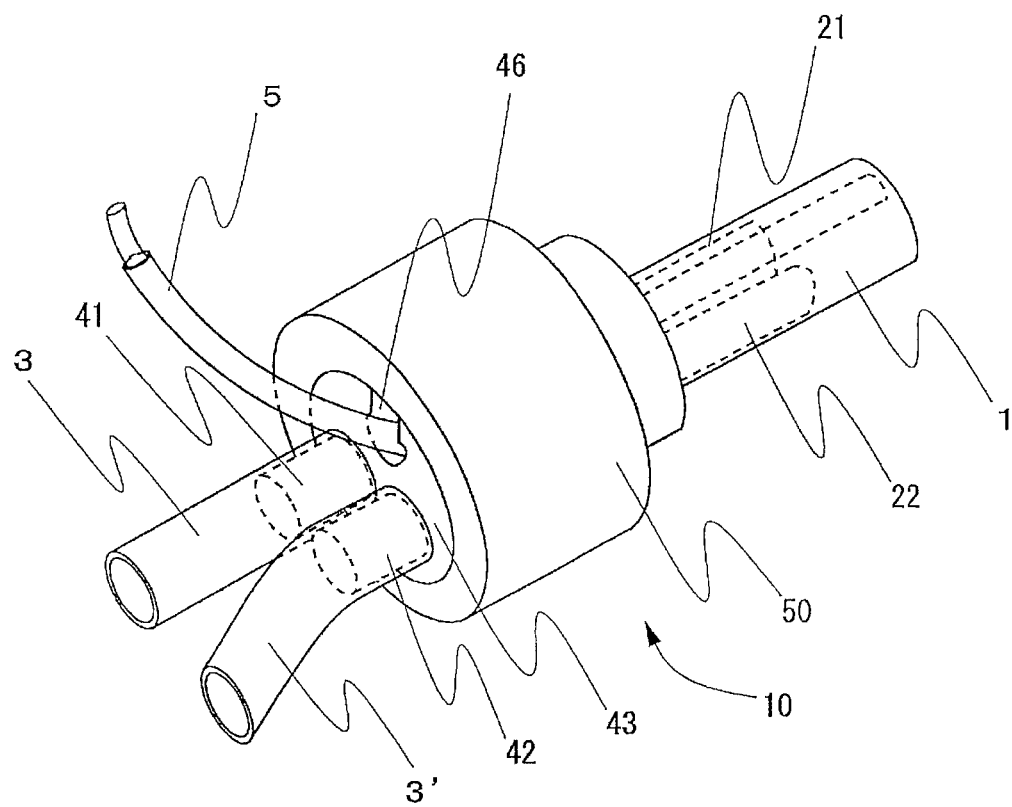
FIG. 5 is a drawing for explaining about an example of use of the adapter in FIG. 2.

In the adapter 10 shown in FIG. 2, the second attachment member 40 is formed with a second cutout 46. When the fixing member 50 is used for fixing, the fixing member 50 covers the first base portion 23 and, consequently, also covers the first cutout 26 formed on the first attachment member 20. Therefore, it is preferable that the second attachment member 40 is formed with the second cutout in order to easily lead the electric wires out. It is possible to form a cutout on the fixing member 50 or the second attachment member 40, depending on the use and the portion to be applied, for leading the electric wires inserted into the multi-lumen tube 1 out. And, in the adapter 10 shown in FIG. 2, the second cutout 46 is formed so that the electric wires can be easily led out. The second cutout 46 makes it possible, as shown in FIG. 5, for the electric wires 5 inserted into the multi-lumen tube 1 to be led out from the second cutout 46 through the first cutout 26 of the first attachment member without being considerably bent. Accordingly, since the electric wires 5 rarely receive any force at a particular portion, it is possible to easily provide the wiring which is unlikely to break.

Although the shape of the second cutout 46 does not have to be limited, it is preferable that the approximate outline in the circumferential direction of the second cutout 46 is substantially the same as the approximate outline in the circumferential direction of the first cutout 26. In addition, in order to have the first cutout 26 communicate with the second cutout 46, the first attachment member 20 and the second attachment member 40 are connected with each other in a way that the first cutout 26 and the second cutout 46 are coaxial. It should be noticed that the packing 30 is not limited as long as the electric wires can be led out from the second cutout 46 through the first cutout 26. As shown in FIG. 2(*b*), the hole of the packing 30 can have a shape similar to that of the first cutout 26 and the second cutout 46.

When the adapter 10 assembled as described above is applied to artificial organs, if a lumen of the multi-lumen tube 1 is connected to the single tube 3 and another lumen is connected to the single tube 3' and electric wires are inserted into the other lumen, the fluid transported into one of the lumens flows into the artificial organs through the first port 21, the second port 41 and the single tube 3. Then, the fluid circulates through the artificial organs, and the circulated fluid is discharged from the artificial organs through the single tube 3', the second port 42 and the first port 22. As mentioned before, if the fluid is a cooling medium such as cooling water, for example, it becomes easy to transport the cooling medium into and from the artificial organs. During the transportation, the first port (inflow port) functions as a port through which the cooling medium flows into and out of the artificial organs, and the second port (discharge port) functions as a port through which the cooling medium flows into the adapter 10 from outside and through which cooling medium is discharged from the adapter 10.

Figure 6:
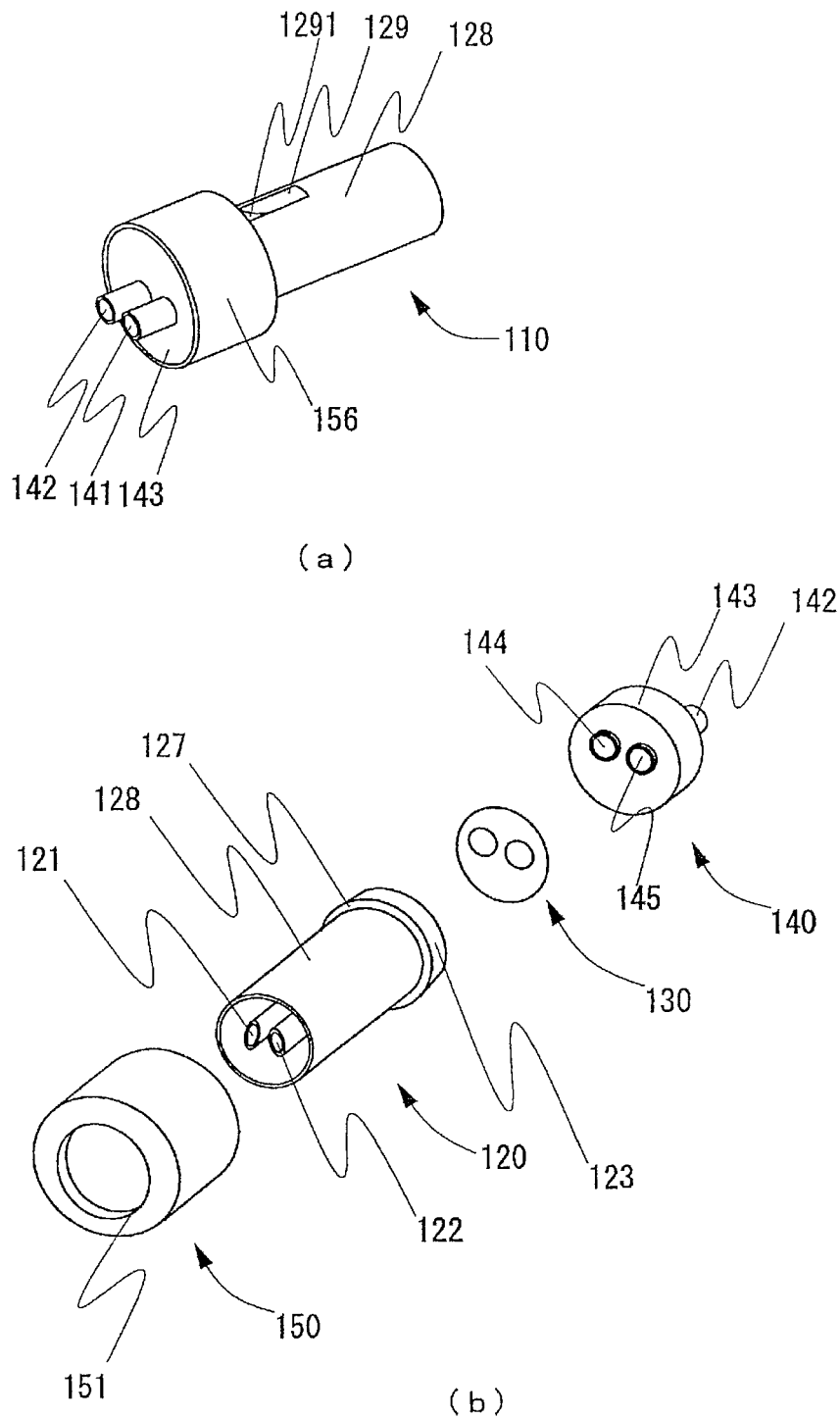
FIG. 6 (a) is a perspective view of the second embodiment of the adapter according to the present invention.

FIG. 6 is a perspective view of the second embodiment of the adapter according to the present invention. An adapter 110 includes, as shown in FIG. 6(*b*), a first attachment member 120, a packing 130, a second attachment member 140 and a fixing member 150. The second attachment member 140 is formed with second openings 144 and 145. The second openings 144 and 145 are disposed on a second base portion 143 of the second attachment member 140 so as to correspond to a first opening portion (not shown) communicating with first ports 121 and 122 provided at a first base portion 123 of the first attachment member 120. When the adapter 110 is to be assembled, first, the first base portion 123 and the second base portion 143 are coaxially assembled such that the first opening portion and the second openings 144 and 145 communicate with each other. Next, the fixing member 150 is fitted from the side of the first port of the first attachment member 120, and then a female thread portion (not shown) inside of the fixing member 150 and a male thread (not shown) formed around the second base portion are screwed with each other. As a result, an inner protrusion 151 provided at a base end of the fixing member 150 and a base portion 127 of the first base portion are engaged, so the adapter 110 is assembled as shown in FIG. 6(*a*). It would be acceptable that, as shown in FIG. 6(*b*), there is a packing 130 between the first attachment member 120 and the second attachment member 140. The packing is not particularly limited as long as the packing prevents the leakage of liquid through any gap at a connection portion between the first attachment member 120 and the second attachment member 140, and as long as the two first ports 121 and 122 communicate with the two second ports 141 (one of them is not shown) through the second openings 144 and 145.

In the adapter 110 shown in FIG. 6(*a*), a cutout 129 through which electric wires inserted in the multi-lumen tube are led out is formed at an outside cover portion 128, which is cylindrically formed around the first ports 121 and 122 of the first base portion 123. As long as the cutout 129 allows the electric wires inserted into one of the lumens of the multi-lumen tube to be led out, the size and the position of the cutout 129 is not particularly limited. However, it is preferable that the cutout 129 is located at a position of the outside cover portion 128 near the first base portion 123 because that makes it easier to lead out the electric wires. It is further preferable that a slanting portion 1291 is formed on the bottom of the cutout 129 for guiding the electric wires toward outside.

As mentioned above, as long as the adapter according to the present invention maintains its function as an adapter, its material is not particularly limited, and it may be obtained with a known manufacturing method. As long as the first attachment member and the second attachment member employ a material which is unlikely to be deformed as a result of the multi-lumen tube and the single tubes being connected to the adapter and the fluid being transported through the adapter, the adapter can be made of metal and hard resin. It is preferable to employ metals which cause less physical impact on living bodies. In addition, as long as the packing has a sealing function, the material of the packing is not limited. The packing can be made of silicone rubber.

As mentioned above, the adapter according to the present invention bundles a plurality of tubes used for transporting fluid into and from the adapter and electric wires for sending the electric power. In addition, since a tube having a transverse section of substantially fan-like lumens is used for decreasing dead space, the shorter diameter decreases the strain on the human bodies, and it becomes easy to realize a division through which power supply and transported fluids are supplied to the artificial organs. Therefore, the above-mentioned adapters 10 and 110 are used for artificial organs, and are used as a connection structure for medical devices including a driving section. In other words, the connection structure is a connection structure for the medical device including an adapter 10 or an adapter 110, and a driving section. The multi-lumen tube includes a first lumen, a second lumen, and a third lumen. The first lumen and the second lumen are formed such that the cooling medium for the driving section can flow therethrough. The third lumen contains the electric wires inserted therein. The connection structure includes two tubes, as individual single tubes, through which the cooling medium can flow. The first lumen and the second lumen communicate with the single tubes respectively such that the cooling medium can flow therethrough. The electric wires can be led out through the first cutout to a product to be electrically connected. The connection structure can be preferably applied to an implantable artificial heart provided with a pump driven especially by power supply because the connection structure is hardly constrained by the device structure of the power supply or for cooling.

The invention claimed is:

1. An artificial organ adapter for connecting a multi-lumen tube and a single tube such that passages of the multi-lumen tube and the single tube communicate with each other, the multi-lumen tube including a plurality of lumens extending in the axial direction, the transverse section of the lumens being oddly formed or deformed, the single tube having a single passage, the adapter comprising:
- a first attachment member to which the multi-lumen tube is attached, and
- a second attachment member to which the single tube is attached,
- the first attachment member includes a plurality of first ports having an outer diameter substantially the same as that of a lumen opening at the end portion of the multi-lumen tube, and a first cutout; the first ports are positioned such that the first ports can fit into the lumen openings when the multi-lumen tube is attached to the first attachment member, and the first cutout is formed in a way so as to correspond to one of the lumen openings when the multi-lumen tube is attached to the first attachment member,
- the second attachment member includes second ports to fit into a lumen of the single tube, the number of the second ports is the same as that of the first ports,
- the plurality of first ports have a substantially elliptic shape to be fitted into the lumen opening in a liquid-tight state,
- the plurality of first ports include a first one of the first ports and a second one of the first ports,
- the first one of the first ports and the second one of the first ports include curved portions at opposite sides thereof in a long diameter direction,
- a distance between one of the curved portions of the first one of the first port and one of the curved portions of the second one of the first ports is shorter than a distance between the other of the curved portions of the first one of the first port and the other of the curved portions of the second one of the first ports, and
- the first cutout is arranged between the other curved portion of the first one of the first ports and the other curved portion of the second one of the first ports.

2. The artificial organ adapter according to claim 1, wherein the first attachment member includes a first base portion, the first base portion having a surface on which the first ports are disposed and an opposite surface on which first opening portions are disposed for communicating with the first ports, the second attachment member includes a second base portion, the second base portion having a surface on which the second ports are disposed and an opposite surface on which second openings are disposed for communicating with the second ports, the first opening portions and the second openings are positioned so as to correspond to each other.

3. The artificial organ adapter according to claim 1, wherein an outer periphery of the second base portion of the second attachment member is formed with a spiral male thread, the first opening portions or the second openings include tubular projections,
- the adapter further comprising a fixing member configured to screw with the male thread, the first opening portions and the second openings are joined to each other for engagement, and the male thread and the fixing member being screwed with each other so that the first attachment member and the second attachment member are fixed to each other.

4. The artificial organ adapter according to claim 1, wherein the second attachment member is formed with a second cutout, and
- the first attachment member and the second attachment member are joined to each other in a way that the first ports, as inflow ports, and the first cutout respectively communicate with the second ports, as discharge ports, and the second cutout.

5. A connection structure for a medical device, the medical device including a driving section, the connection structure comprising an artificial organ adapter according to claim 1, wherein
- the multi-lumen tube includes a first lumen, a second lumen, and a third lumen, the first lumen and the second lumen are formed such that a cooling medium for the driving section can flow therethrough, and the third lumen contains electric wires inserted therethrough,
- the connection structure further comprising two tubes as the single tube through which the cooling medium can flow,
- the first lumen and the second lumen communicate respectively with the single tubes such that the cooling medium can flow therethrough, and
- the electric wires are led out from the first cutout to a product to be electrically connected.

6. The artificial organ adapter according to claim 2, wherein an outer periphery of the second base portion of the second attachment member is formed with a spiral male thread, the first opening portions or the second openings include tubular projections,
- the adapter further comprising a fixing member configured to screw with the male thread, the first opening portions and the second openings are joined to each other for engagement, and the male thread and the fixing member being screwed with each other so that the first attachment member and the second attachment member are fixed to each other.

7. The artificial organ adapter according to claim 2, wherein the second attachment member is formed with a second cutout, and
- the first attachment member and the second attachment member are joined to each other in a way that the first ports, as inflow ports, and the first cutout respectively communicate with the second ports, as discharge ports, and the second cutout.

8. The artificial organ adapter according to claim 3, wherein the second attachment member is formed with a second cutout, and
- the first attachment member and the second attachment member are joined to each other in a way that the first ports, as inflow ports, and the first cutout respectively communicate with the second ports, as discharge ports, and the second cutout.

9. The artificial organ adapter according to claim 6, wherein the second attachment member is formed with a second cutout, and
- the first attachment member and the second attachment member are joined to each other in a way that the first ports, as inflow ports, and the first cutout respectively communicate with the second ports, as discharge ports, and the second cutout.

10. A connection structure for a medical device, the medical device including a driving section, the connection structure comprising an artificial organ adapter according to claim 2, wherein
- the multi-lumen tube includes a first lumen, a second lumen, and a third lumen, the first lumen and the second lumen are formed such that a cooling medium for the driving section can flow therethrough, and the third lumen contains electric wires inserted therethrough,
- the connection structure further comprising two tubes as the single tube through which the cooling medium can flow, the first lumen and the second lumen communicate respectively with the single tubes such that the cooling medium can flow therethrough, the electric wires are led out from the first cutout to a product to be electrically connected.

11. A connection structure for a medical device, the medical device including a driving section, the connection structure comprising an artificial organ adapter according to claim 3, wherein the multi-lumen tube includes a first lumen, a second lumen, and a third lumen, the first lumen and the second lumen are formed such that a cooling medium for the driving section can flow therethrough, and the third lumen contains electric wires inserted therethrough, the connection structure further comprising two tubes as the single tube through which the cooling medium can flow, the first lumen and the second lumen communicate respectively with the single tubes such that the cooling medium can flow therethrough, the electric wires are led out from the first cutout to a product to be electrically connected.

12. A connection structure for a medical device, the medical device including a driving section, the connection structure comprising an artificial organ adapter according to claim 4, wherein the multi-lumen tube includes a first lumen, a second lumen, and a third lumen, the first lumen and the second lumen are formed such that a cooling medium for the driving section can flow therethrough, and the third lumen contains electric wires inserted therethrough, the connection structure further comprising two tubes as the single tube through which the cooling medium can flow, the first lumen and the second lumen communicate respectively with the single tubes such that the cooling medium can flow therethrough, the electric wires are led out from the first cutout to a product to be electrically connected.

13. A connection structure for a medical device, the medical device including a driving section, the connection structure comprising an artificial organ adapter according to claim 6, wherein the multi-lumen tube includes a first lumen, a second lumen, and a third lumen, the first lumen and the second lumen are formed such that a cooling medium for the driving section can flow therethrough, and the third lumen contains electric wires inserted therethrough, the connection structure further comprising two tubes as the single tube through which the cooling medium can flow, the first lumen and the second lumen communicate respectively with the single tubes such that the cooling medium can flow therethrough, the electric wires are led out from the first cutout to a product to be electrically connected.

14. A connection structure for a medical device, the medical device including a driving section, the connection structure comprising an artificial organ adapter according to claim 7, wherein the multi-lumen tube includes a first lumen, a second lumen, and a third lumen, the first lumen and the second lumen are formed such that a cooling medium for the driving section can flow therethrough, and the third lumen contains electric wires inserted therethrough, the connection structure further comprising two tubes as the single tube through which the cooling medium can flow, the first lumen and the second lumen communicate respectively with the single tubes such that the cooling medium can flow therethrough, the electric wires are led out from the first cutout to a product to be electrically connected.

15. A connection structure for a medical device, the medical device including a driving section, the connection structure comprising an artificial organ adapter according to claim 8, wherein the multi-lumen tube includes a first lumen, a second lumen, and a third lumen, the first lumen and the second lumen are formed such that a cooling medium for the driving section can flow therethrough, and the third lumen contains electric wires inserted therethrough, the connection structure further comprising two tubes as the single tube through which the cooling medium can flow, the first lumen and the second lumen communicate respectively with the single tubes such that the cooling medium can flow therethrough, the electric wires are led out from the first cutout to a product to be electrically connected.

16. A connection structure for a medical device, the medical device including a driving section, the connection structure comprising an artificial organ adapter according to claim 9, wherein the multi-lumen tube includes a first lumen, a second lumen, and a third lumen, the first lumen and the second lumen are formed such that a cooling medium for the driving section can flow therethrough, and the third lumen contains electric wires inserted therethrough, the connection structure further comprising two tubes as the single tube through which the cooling medium can flow, the first lumen and the second lumen communicate respectively with the single tubes such that the cooling medium can flow therethrough, the electric wires are led out from the first cutout to a product to be electrically connected.

17. The artificial organ adapter according to claim 1, wherein in the multi-lumen tube, the transverse section of the lumens has substantially a fan shape.

\* \* \* \* \*